US012171942B2

(12) United States Patent
Collins et al.

(10) Patent No.: US 12,171,942 B2
(45) Date of Patent: Dec. 24, 2024

(54) RESPIRATORY MASK SYSTEM

(71) Applicant: Fisher & Paykel Healthcare Limited, Auckland (NZ)

(72) Inventors: Janine Elizabeth Collins, Auckland (NZ); Max Leon Betteridge, Auckland (NZ); Vitaly Kapelevich, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/332,492

(22) Filed: Jun. 9, 2023

(65) Prior Publication Data
US 2024/0082524 A1     Mar. 14, 2024

Related U.S. Application Data

(63) Continuation of application No. 16/640,695, filed as application No. PCT/IB2018/056297 on Aug. 21, 2018, now Pat. No. 11,717,627.
(Continued)

(51) Int. Cl.
*A61M 16/06* (2006.01)
*A61M 16/08* (2006.01)
*A61M 39/10* (2006.01)

(52) U.S. Cl.
CPC .... *A61M 16/0616* (2014.02); *A61M 16/0683* (2013.01); *A61M 16/0816* (2013.01);
(Continued)

(58) Field of Classification Search
CPC .......... A61M 16/0616; A61M 16/0605; A61M 16/0611; A61M 16/0622; A61M 16/0633;
(Continued)

(56) References Cited

U.S. PATENT DOCUMENTS 4,969,879 A    11/1990   Lichte
11,717,627 B2   8/2023   Collins et al.
(Continued)

FOREIGN PATENT DOCUMENTS

CN        205885937     1/2017
WO     WO 2019/038662   2/2019

*Primary Examiner* — Joseph D. Boecker
*Assistant Examiner* — Brian T Khong
(74) *Attorney, Agent, or Firm* — VIA LLP

(57) ABSTRACT

A respiratory mask includes a frame and a cushion module including a housing and a cushion that seals on a user's face in use. The housing includes a first connector, for example, a female connector, and the frame includes a second connector, for example, a male connector. The first and second connectors are coupled together in use. The housing includes one or more fasteners that secure the male connector to the female connector. Each fastener includes a base portion coupled to the housing and a moveable portion pivotally connected to the base portion. To assemble the mask, the male connector is inserted into the female connector such that the male connector engages the fasteners. Advancement of the male connector into the female connector causes the fasteners to change orientation from a neutral position to a toggled position and compress. The compressed fasteners apply a retention force to the male connector.

23 Claims, 14 Drawing Sheets

Related U.S. Application Data

(60) Provisional application No. 62/549,273, filed on Aug. 23, 2017.

(52) U.S. Cl.
CPC .... *A61M 39/1011* (2013.01); *A61M 39/1055* (2013.01); *A61M 2039/1044* (2013.01); *A61M 2039/1083* (2013.01); *A61M 2205/0216* (2013.01)

(58) Field of Classification Search
CPC .......... A61M 16/0683; A61M 16/0816; A61M 16/0825; A61M 16/0875; A61M 39/10; A61M 39/1011; A61M 39/1055; A61M 2039/1027; A61M 2039/1044; A61M 2039/1083; A61M 2039/1088
See application file for complete search history.

(56) References Cited

U.S. PATENT DOCUMENTS

| | | | |
|---|---|---|---|
| 2006/0201514 A1* | 9/2006 | Jones | A61M 16/0683 128/206.24 |
| 2008/0264413 A1 | 10/2008 | Doherty et al. | |
| 2012/0153613 A1 | 6/2012 | Kauppi et al. | |
| 2014/0238389 A1 | 8/2014 | Bruggemann et al. | |
| 2015/0217074 A1 | 8/2015 | Wells et al. | |
| 2016/0067440 A1 | 3/2016 | Matsubara et al. | |
| 2016/0074610 A1 | 3/2016 | Rubin | |

\* cited by examiner

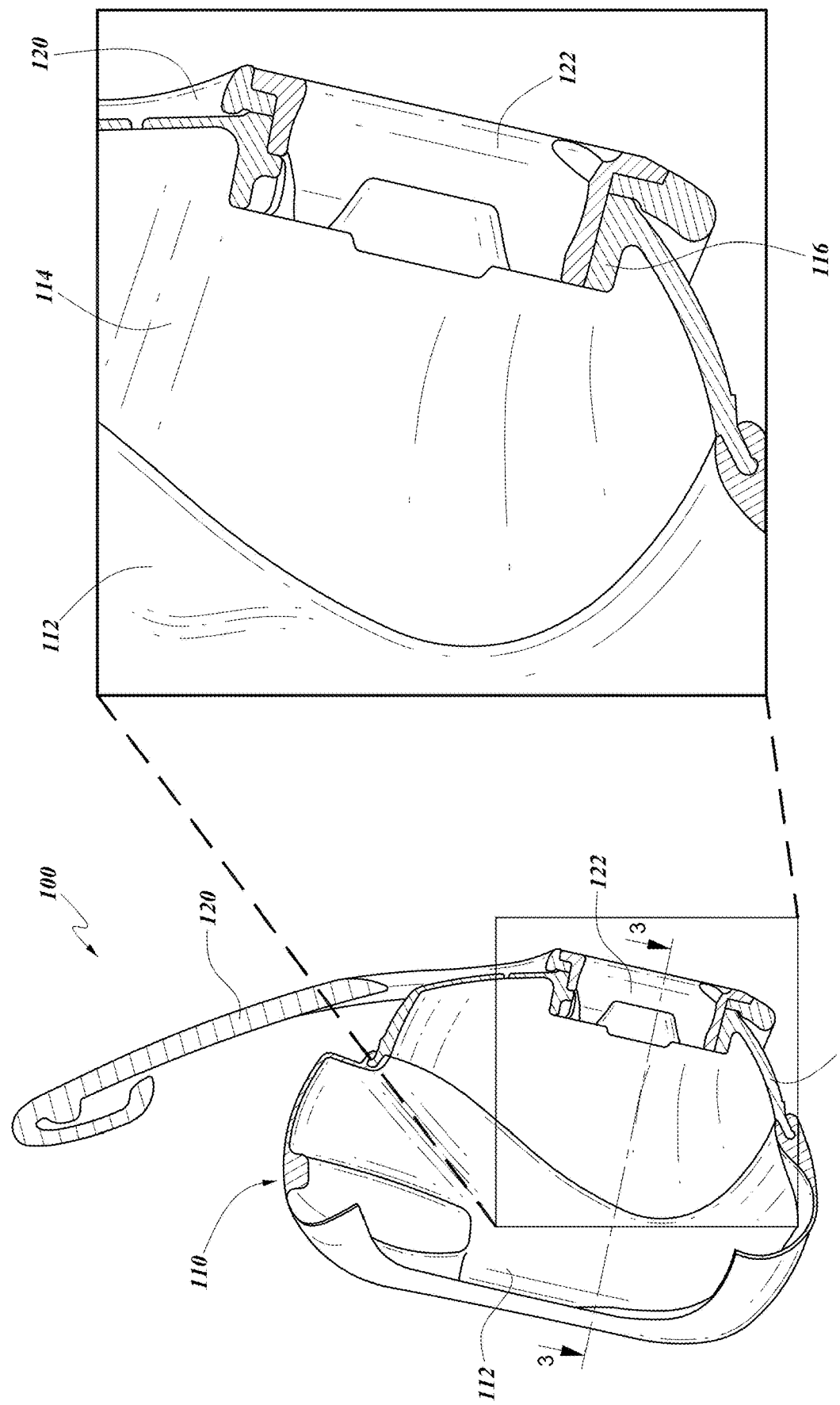

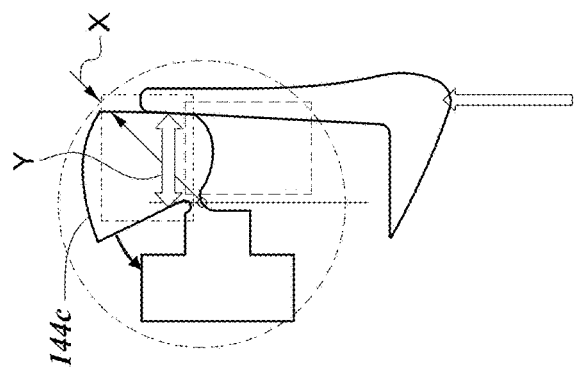
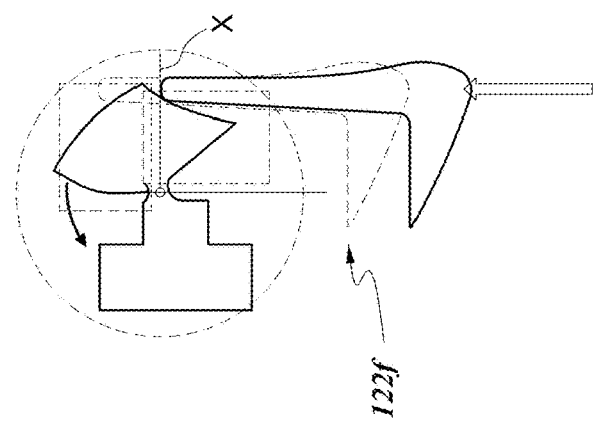
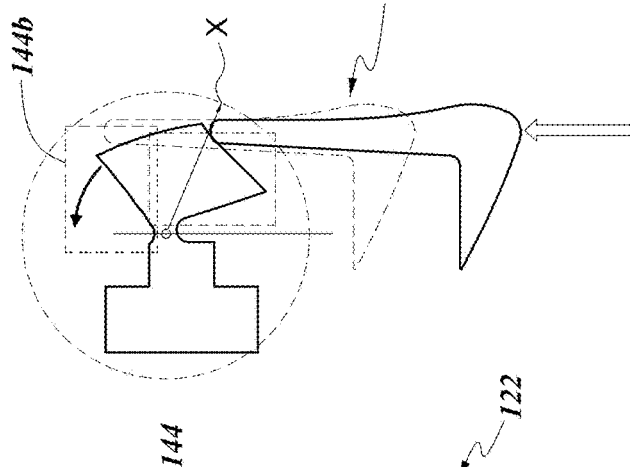
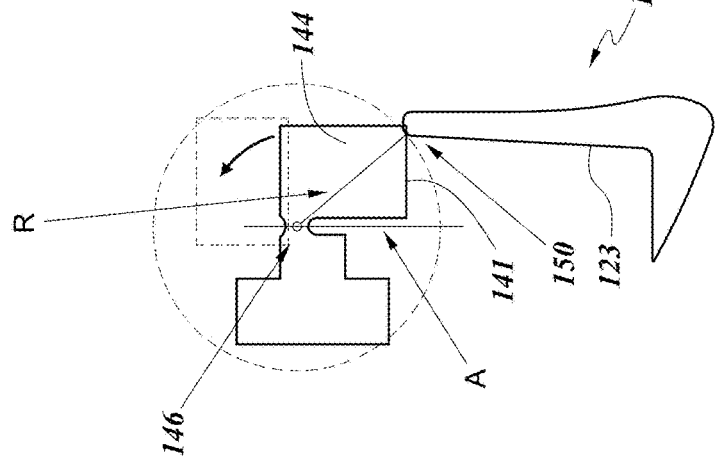

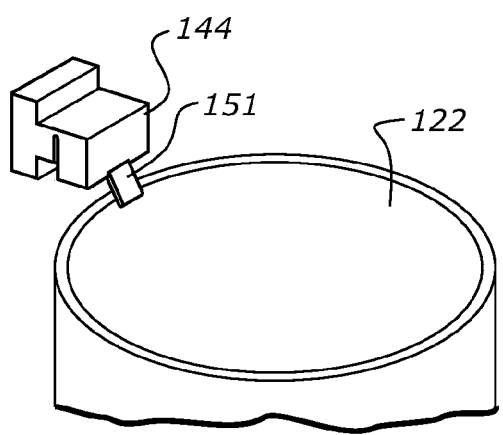
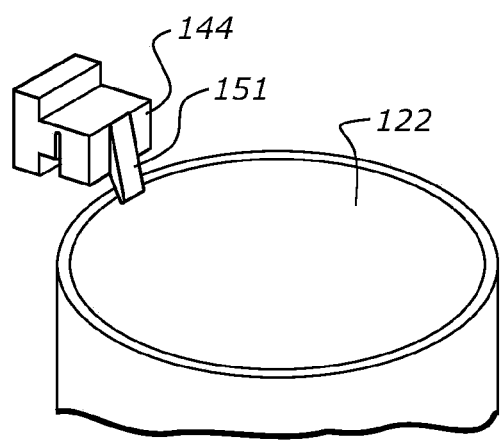
FIG. 15A  FIG. 15B

RESPIRATORY MASK SYSTEM

INCORPORATION BY REFERENCE TO ANY PRIORITY APPLICATIONS

This application is a continuation of U.S. patent application Ser. No. 16/640,695, filed Feb. 20, 2020 which is a 371 application of PCT Application No. PCT/IB2018/056297, filed Aug. 21, 2018, which claims priority from U.S. provisional application 62/549,273 filed Aug. 23, 2017, the entire contents of which are hereby incorporated by reference.

BACKGROUND

Field

The present disclosure generally relates to a respiratory mask system for the delivery of respiratory therapy to a patient. More particularly, the present disclosure relates to various components of a respiratory mask system.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that forms an airtight seal in or around the patient's nose and/or mouth. Respiratory masks are available in a range of styles including full-face, nasal, direct nasal and oral masks, which create an airtight seal with the nose and/or mouth. The seal or cushion is held in place on the patient's face by the headgear. In order to maintain an airtight seal the headgear should provide support to the patient interface such that it is held in a stable position relative to the patient's face during use. Such respiratory masks may also be used to deliver NIV and other therapies.

SUMMARY

The systems and devices described herein have innovative aspects, no single one of which is indispensable or solely responsible for their desirable attributes. Without limiting the scope of the claims, some of the advantageous features will now be summarized.

In some aspects, a respiratory mask includes a first component, a second component, and at least one fastener. The first component has a first connector defining an opening. The second component has a second connector. The opening of the first connector is configured to receive the second connector to couple the first and second components. The at least one fastener is configured to retain the first and second connectors together. Each fastener includes a base portion fixed to the first component and a moveable portion pivotally coupled to the base portion via a joint. The moveable portion is configured to pivot about the joint from a neutral orientation to a locked orientation when the second connector is coupled to the first connector. In the locked orientation, the moveable portion applies a retention force to the second connector to secure the second connector to the first connector.

The moveable portion can be made of a resilient deformable material and configured to be compressed as the moveable portion is pivoted from the neutral orientation to the locked orientation. Compression of the moveable portion can provide the retention force to the second connector. The moveable portion can be more compressed in an intermediate orientation between the neutral orientation and the locked orientation than in both the neutral orientation and the locked orientation. The moveable portion can be more compressed in the locked orientation than in the neutral orientation. The moveable portion can be biased toward the neutral orientation.

The mask can further include a plurality of fasteners spaced about the opening of the first connector. A distance between an inner surface of the moveable portion of a first fastener and an inner surface of the moveable portion of a second fastener that is disposed opposite the first fastener across the opening is less than a width of the second connector.

The joint can include a living hinge. The living hinge can include a thinned portion of material extending between the base portion and the moveable portion.

The base portion and moveable portion can be integrally formed.

The moveable portion can include a contact point spaced from the joint, and the contact point can be configured to be engaged by the second connector when the second connector is coupled to the first connector. A distance between the joint and the contact point in the neutral orientation can be greater than the distance in an intermediate orientation between the neutral orientation and the locked orientation and greater than or equal to the distance in the locked orientation. The distance in the intermediate orientation can be less than the distance in the locked orientation.

A distal edge of the moveable portion that faces a mouth of the opening and is configured to contact the second connector can be flat.

The first component can include a housing coupled to a cushion configured to seal on a user's face in use. The first connector can include a generally cylindrical female connector. The second component can include a frame. The second connector can include a generally cylindrical male connector configured to be received in the female connector. The base portion can be overmolded to the housing.

In some aspects, a respiratory mask includes a first component, a second component, and at least one fastener. The first component has a first connector defining an opening. The second component has a second connector. The opening of the first connector is configured to receive the second connector to couple the first and second components. The at least one fastener is configured to retain the first and second connectors together. Each fastener includes a fixed portion and a moveable portion coupled to the fixed portion.

The moveable portion has a first side and a second side. The moveable portion is configured to rotate when the second connector is coupled to the first connector from a first position in which the first side faces the opening to a second position in which the second side faces the opening.

The moveable portion can be made of a resiliently deformable material and configured to be compressed as the moveable portion is rotated from the first position to the second position. The moveable portion can be more compressed in an intermediate position between the first position and the second position than in both the first position and the second position. The moveable portion can be more compressed in the second position than in the first position.

The mask can include a plurality of fasteners spaced about the opening of the first connector. The moveable portion can be biased toward the first position. The fixed portion and moveable portion can be integrally formed. The first side of the moveable portion can be flat.

The first component can include a housing coupled to a cushion configured to seal on a user's face in use. The first connector can include a generally cylindrical female connector. The second component can include a frame. The second connector can include a generally cylindrical male connector configured to be received in the female connector. The fixed portion can be overmolded to the housing.

In some aspects, a respiratory mask includes a first component, a second component, and at least one fastener. The first component has a first connector defining an opening. The second component has a second connector. The opening of the first connector is configured to receive the second connector to couple the first and second components. The at least one fastener is configured to retain the first and second connectors together. The fastener is configured to pivot from a neutral orientation to a locked orientation when the second connector is coupled to the first connector. In the locked orientation, the moveable portion applies a retention force to the second connector to secure the second connector to the first connector.

The fastener can be made of a resiliently deformable material and configured to be compressed as the fastener is pivoted from the neutral orientation to the locked orientation. Compression of the fastener can provide the retention force to the second connector. The fastener can be more compressed in an intermediate orientation between the neutral orientation and the locked orientation than in both the neutral orientation and the locked orientation. The fastener can be more compressed in the locked orientation than in the neutral orientation.

The mask can include a plurality of fasteners spaced about the opening of the first connector. A distance between an inner surface of a first fastener and an inner surface of a second fastener that is disposed opposite the first fastener across the opening can be less than a width of the second connector.

A distal edge of the fastener that faces a mouth of the opening and is configured to contact the second connector is flat.

The first component can include a housing coupled to a cushion configured to seal on a user's face in use. The first connector can include a generally cylindrical female connector. The second component can include a frame. The second connector can include a generally cylindrical male connector configured to be received in the female connector.

In various embodiments the mask may comprise at least one alignment feature adapted to guide a first component, preferably a housing of a first component, into alignment with a second component, preferably a frame of the second component.

In various embodiments the mask may comprise a first component having a first connector and a second component having a second connector.

In various embodiments the mask may comprise at least one alignment feature adapted to align or guide the second connector, preferably the male connector, into the first connector, preferably the female connector, during assembly.

In various embodiments the mask may comprise a fastener configured to retain the first and second connectors together.

In various embodiments the fastener may comprise a base portion and a moveable portion.

In various embodiments the moveable portion of the fastener may comprise at least one alignment feature adapted to align or guide the male connector into the female connector during assembly.

In various embodiments the alignment feature may guide the second connector, preferably the male connector, into alignment with the moveable portion of the at least one fastener.

In various embodiments the at least one alignment feature may be in the form of a flap, finger or protrusion or any other form adapted to align or guide the first and second connectors during assembly.

BRIEF DESCRIPTION OF THE DRAWINGS

FIG. 1 illustrates a section view of an example embodiment of a mask.

FIG. 2 illustrates an enlarged portion of the mask of FIG. 1.

FIGS. 9AA, 9BB, 9CC, and 9DD illustrate rotation and compression of the moveable portion during various stages of insertion of the male connector into the housing as well as the neutral orientation and uncompressed toggled position for reference.

FIGS. 15A and B show perspective views of part of a mask in accordance with an embodiment of the invention in which the mask comprises an alignment feature.

DETAILED DESCRIPTION

Figure 3:
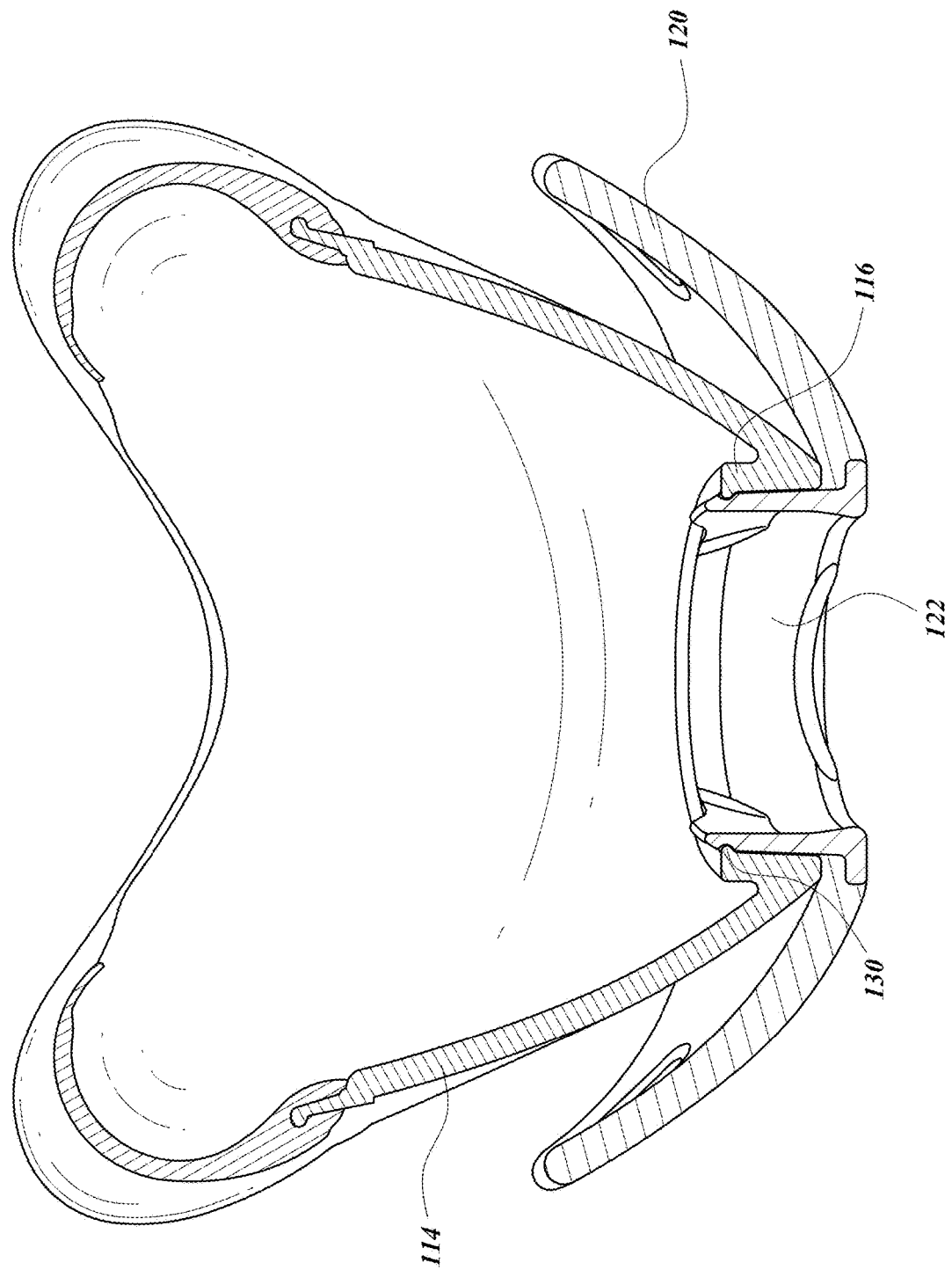
FIG. 3 illustrates a section view of the mask taken along line 3-3 in FIG. 1.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

A respiratory mask can include two or more components that are coupled together in use. For example, FIGS. 1-3 illustrate an example embodiment of a mask 100 including a cushion module 110 that includes a seal or cushion 112 that seals around the user's nose and/or mouth in use and a frame 120 that connects the cushion module 110 to headgear and/or a gas delivery conduit. The cushion module 110 can include the seal or cushion 112 and a housing 114 that connects the seal or cushion 112 to the frame 120 and/or a gas delivery conduit. The housing 114 can be relatively more rigid than the seal or cushion 112. The cushion module 110, e.g., the housing 114, can be connected to the frame 120 via a snap-fit connection. In the embodiment of FIGS. 1-3, the frame 120 includes a connector, which in the illustrated arrangement is a cylindrical or generally cylindrical male connector 122 projecting from a rear (toward the left of FIG. 1 and toward the user's face in use) of the frame 120. However, other suitable shapes can also be used. Non-circular shapes provide an advantage of inhibiting or preventing relative rotation between the cushion module 110 and the frame 120. A front (toward the right of FIG. 1 and away from the user's face in use) of the housing 114 includes a complementary (e.g., cylindrical or generally cylindrical) female connector 116 defining a central opening and sized and shaped to concentrically receive the male connector 122. In other embodiments, the housing 114 can include a male connector and the frame 120 can include a female connector. In use, a gas supply conduit can be received in and/or coupled to the male connector 122 to deliver gases to the mask 100. Alternatively, the gas supply conduit can be carried by the cushion module 110, e.g., the housing 114.

FIGS. 1-3 illustrate an arrangement in which the male connector 122 couples to the female connector 116 via a snap fit connection 130. For example, the female connector 116 can include one or more bumps or protrusions extending inwardly from an inner surface of the female connector 116, and the male connector 122 can include one or more corresponding recesses in an outer surface of the male connector configured to receive the bumps or protrusions of the female connector 116 to form the snap fit connection 130, as shown in FIG. 3.

The present disclosure relates to an alternative connection mechanism or means to couple the frame 120 to the cushion module 110, e.g., the housing 114. In other respects, the mask 100 of FIGS. 4-12C can be the same as or similar to the mask 100 of FIGS. 1-3. Preferably, the mask 100 of FIGS. 4-12C includes a feedback and/or retention arrangement that provides feedback to the user relating to the assembly of the cushion module 110 to the frame 120 and/or operates to provide a portion or an entirety of a retention or connection force between the cushion module 110 and the frame 120. The feedback can be tactile and/or audible and can indicate to the user that the assembly of the cushion module 110 to the frame 120 is correct or complete.

Figure 4:
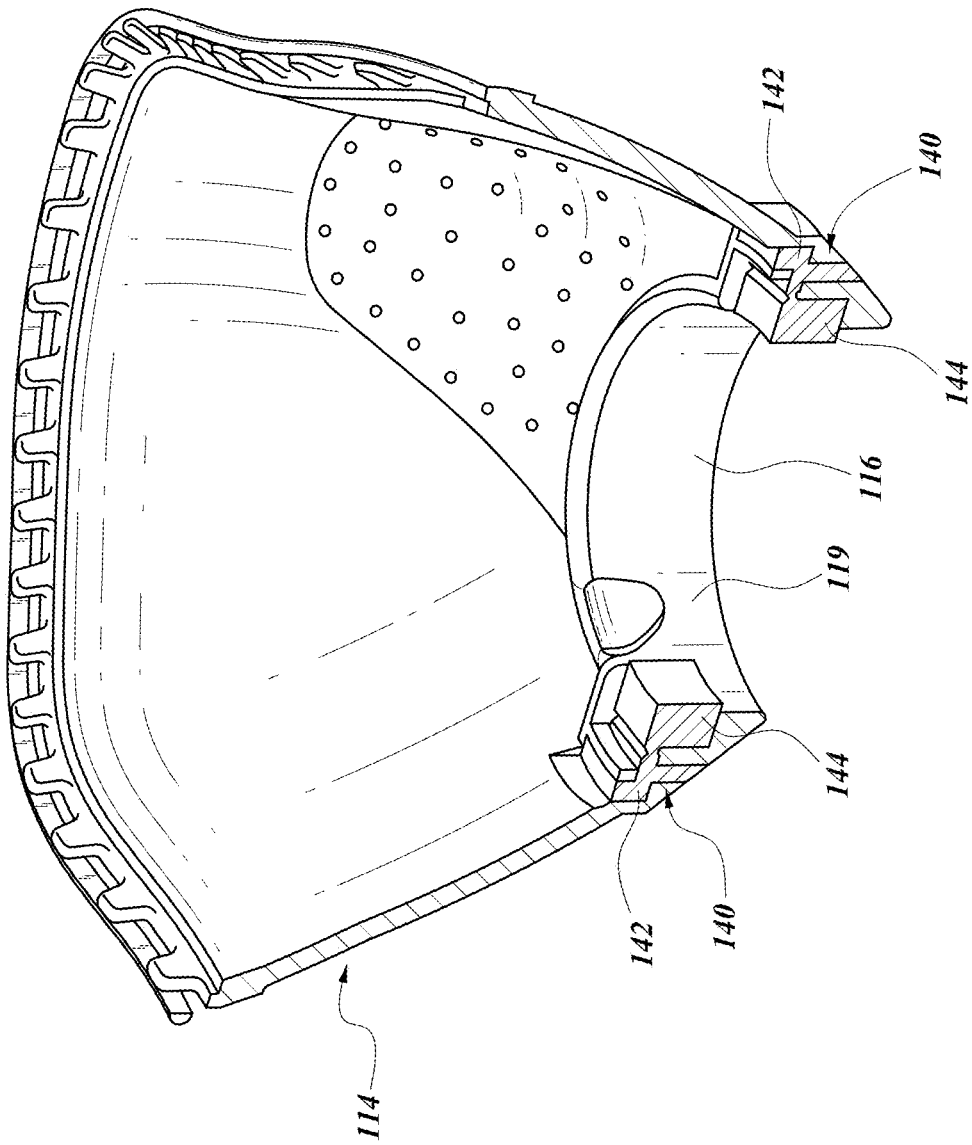
FIG. 4 illustrates a perspective section view of a housing of a cushion module of an example embodiment of a mask.
Figure 5:
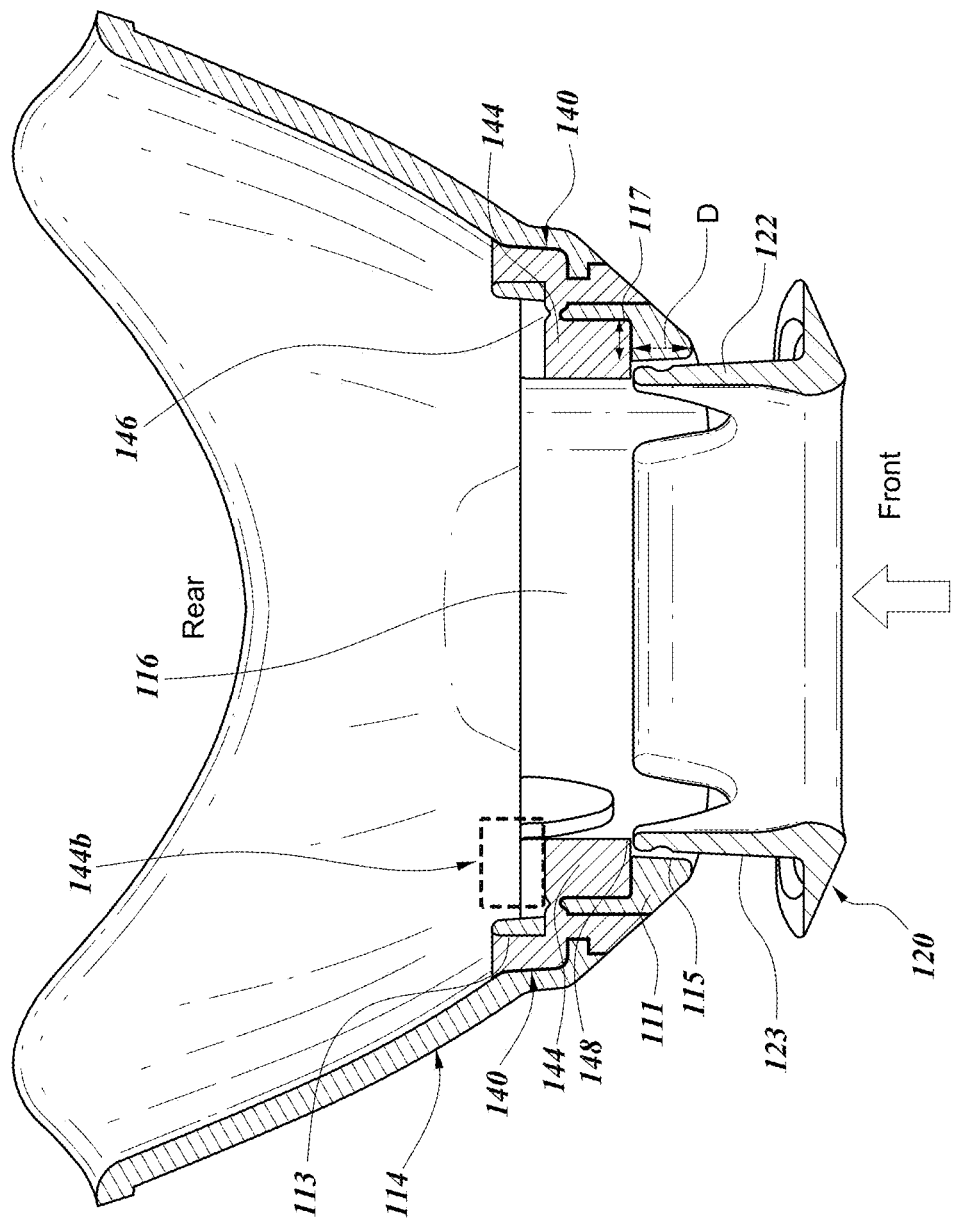
FIG. 5 illustrates a male connector of a frame being inserted into the housing of FIG. 4.
Figure 6:
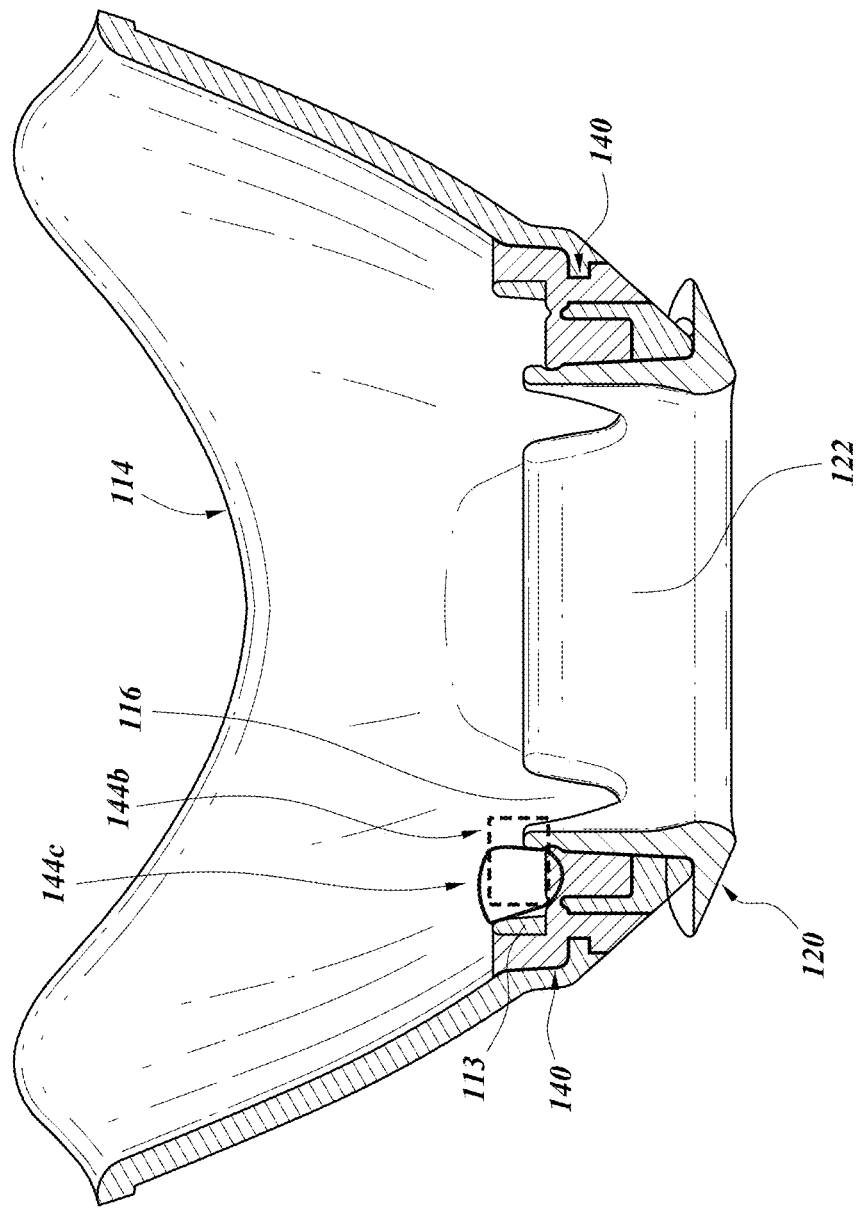
FIG. 6 illustrates the male connector of FIG. 5 fully inserted into the housing of FIGS. 4-5.

As shown in FIGS. 4-6, the mask 100 can include one or more feedback members, retention members, or fasteners 140 (hereinafter referred to as "fasteners" for convenience) that couple the frame 120 to the cushion module 110, e.g., the housing 114. In the illustrated embodiment, each fastener 140 includes a base or fixed portion 142 and a moveable portion 144 that is moveable relative to the base portion 142 and the housing 114. The fastener 140 can include a necked region 139 extending between and/or connecting the base portion 142 and the moveable portion 144. The base portion 142 is larger than, e.g., has at least one dimension that is larger than a corresponding dimension of, the necked region 139. In some embodiments, the moveable portion is a toggle portion that can move or toggle relative to the base portion 142 and the housing 114. The fasteners 140, or at least the moveable portions 144, are made of a material that is compressible, resilient, and provides friction between the fastener 140 and male connector 122, for example, silicone or a thermoplastic elastomer (TPE). The base portion 142, necked region 139, and/or moveable portion 144 can be integrally formed as shown. The base portion 144 is coupled to and/or retained in or by the housing 114. In some embodiments, the base portion 142 is coupled to the housing 114 via, e.g., a snap fit, push fit, or friction fit. In the illustrated embodiment, the base portion 142 is coupled or immovably secured, e.g., over-molded, to the housing 114.

As shown in FIG. 5, the housing 114 can include a retention wall or rib 113 that partially defines a cavity for the base portion 142. A portion of the base portion 142 can be disposed between the rib 113 and a main or outer wall of the housing 114. Another portion of the base portion 142 can be disposed between the outer wall of the housing 114 and a lower wall portion 111 that partially defines the female connector 116. In other embodiments, for example, embodiments in which the housing 114 includes a male connector and the frame 120 includes a female connector, the fastener 140, e.g., the base portion 142, may be coupled or secured to frame 120. In some embodiments, the fastener 140 may include only the moveable portion 144 without a base portion 142, and may be restrained from falling out of the housing 114 (or frame 120) when the cushion module 110 is not yet connected to the frame 120 via other structures or arrangements, for example, a retaining wall or rib.

In the illustrated embodiment, the fastener 140 is positioned such that the moveable portion 144 is disposed along or at least partially aligned with the female connector 116. As shown in FIG. 5, when the frame 120 is not coupled to the housing 114, the moveable portion 144 is partially disposed in a recess 117 in the female connector 116 extending outwardly from an inner surface 119 of the female connector 116. An inner portion of the moveable portion 144 extends radially inwardly into the central opening of the female connector 116 to form an overhanging lip 148 along a bottom edge 141 (shown in FIG. 9A) of the moveable portion 144. The edge 141 can also be referred to as a distal, exposed, or facing edge because the edge 141 faces or is exposed to a mouth of the opening of the female connector 116 and is distal relative to the hinge 146. The edge 141 can also be referred to as a radial edge because at least a portion of the edge extends in a radial direction relative to an axis of the opening of the female connector 116 and/or the insertion direction of the male connector 122. The moveable portion 144 is offset or spaced from a front edge of the female connector 116 by a distance D. In at least some embodiments the portion of the inner surface of the female connector 116 extending from the front edge to the recess 117 and/or moveable portion 144 acts as a guide surface 115 as described in greater detail herein.

In the illustrated embodiment, the mask 100 includes two diametrically opposed fasteners 140, e.g., located 180° apart from each other around the female connector 116. In other embodiments, the mask 100 can include more than two fasteners 140. In some embodiments, the fasteners 140 are preferably symmetrically or evenly spaced around the female connector 116 so that the male connector 122 can be evenly aligned with the fasteners 140 during assembly. In some embodiments, the fastener 140 can be in the shape or form of a ring or partial ring that extends around an entirety of the female connector 116 or portion thereof.

Figure 7:
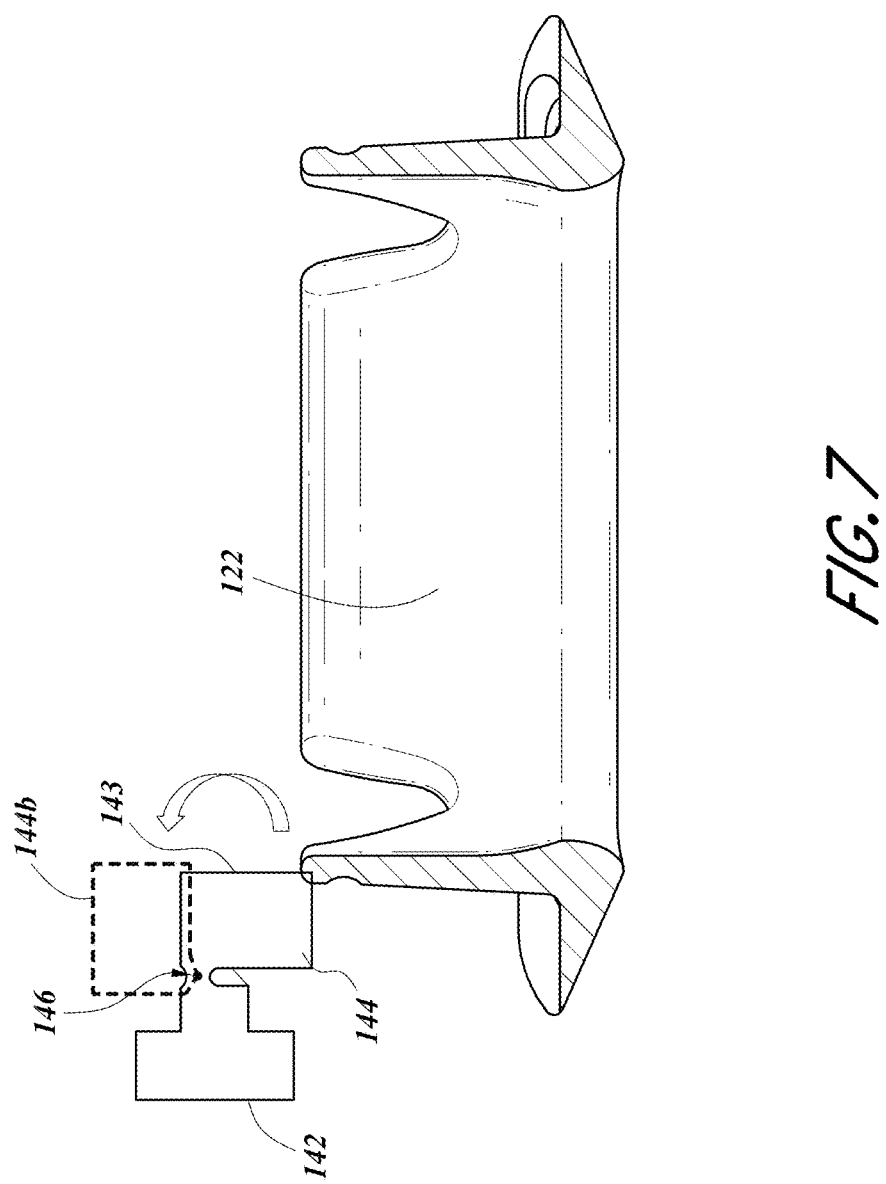
FIG. 7 shows the male connector of FIG. 5 and a fastener of the housing of FIGS. 4-5.

A joint between the base portion 142 and the moveable portion 144 forms or includes a hinge that can define a hinge region or hinge point 146, shown in, for example, FIGS. 5 and 7. The term hinge point is used for convenience in the context of the illustrated two-dimensional sectional views. However, as used herein, the term hinge point is intended to broadly cover various types of hinge structures, such as those having a discrete hinge axis and those in which the hinge movement occurs along a length or width, unless otherwise indicated. In the illustrated embodiment, the base portion 142 and moveable portion 144 are joined by a living hinge that forms or includes the hinge point 146. In other words, the joint between the base portion 142 and moveable portion 144 is made of the same material as the base portion 142 and moveable portion 144. The living hinge is thinned to allow relative movement between the moveable portion 144 and base portion 142. The moveable portion 144 can move, rotate, or pivot about the hinge point 146 relative to the base portion 142. For example, if the base portion 142 is fixed or held stationary in the position shown in FIG. 5, and without any other constraints on the fastener 140, the moveable portion 144 can be moved, rotated, or pivoted from a neutral position or orientation as illustrated in FIG. 5 to a toggled or locked position or orientation approximately indicated by outline 144b.

The moveable portion 144 is bistable or over-centre. In other words, the fastener 140 or moveable portion 144 is stable in both the neutral position (indicated by element 144 in FIGS. 5 and 7) and in the toggled position (indicated by outline 144b in FIGS. 5 and 7). Work or a force above a threshold must be applied to the moveable portion 144 to move the moveable portion 144 from the neutral position over-centre to the toggled position. As the moveable portion 144 is moved from the neutral position, once the center of mass of the moveable portion 144 crosses the hinge point 146, the moveable portion biases toward the toggled position. In embodiments comprising a living hinge, the moveable portion 144 may rely on the presence of the male connector 122 to be stable. That is, deformation of the living hinge when the moveable portion 144 is in the toggled position 144b may produce a force tending to return the moveable portion 144 to the neutral position in the absence of the male connector 122, but which provides a retention force in the presence of the male connector 122.

In the illustrated embodiment, the moveable portion 144 is rectangular in a sectional view. The rectangular shape can advantageously help bias the moveable portion 144 to change orientation to the toggled position when moved over-centre, compared to, for example, a square shape. A rectangular shape can help provide a greater retention force when in the toggled position as the longer dimension (or length) of the rectangle can provide or cause greater compression of the moveable portion 144 in the toggled position as discussed in greater detail herein. Other shapes for the moveable portion 144 are also possible. The flat sides of both square and rectangular moveable portions 144 can advantageously provide the user with haptic feedback that the components are fully connected when the moveable portion 144 reaches the toggled position and the flat side becomes flush with an outer surface 123 (shown in, e.g., FIG. 5) of the male connector 122. Curved, partially curved, and/or asymmetric shapes are also possible. In some embodiments, at least one side or edge of the moveable portion 144 is flat. For example, in some embodiments, at least the bottom edge 141 of the moveable portion 144, which faces the mouth of the opening of the female connector 116, is flat such that the bottom edge 141 can be flush with the outer surface 123 (shown in, e.g., FIG. 5) of the male connector 122 in the toggled position. The moveable portion 144 can rotate about any point or axis of rotation (including a center point or axis), which may or may not be located on the moveable portion 144.

Figure 10:
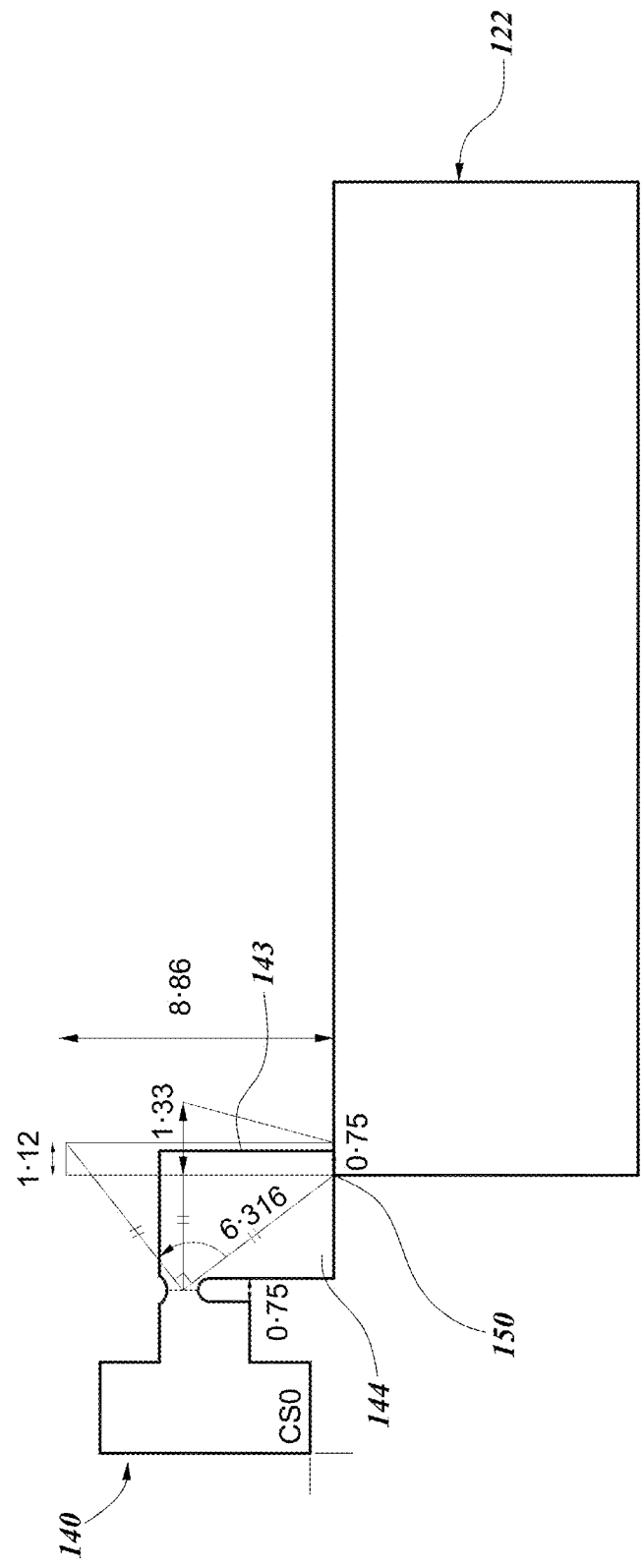
FIG. 10 illustrates compression of the moveable portion relative to its angle of rotation for an example embodiment of the fastener.
Figure 11:
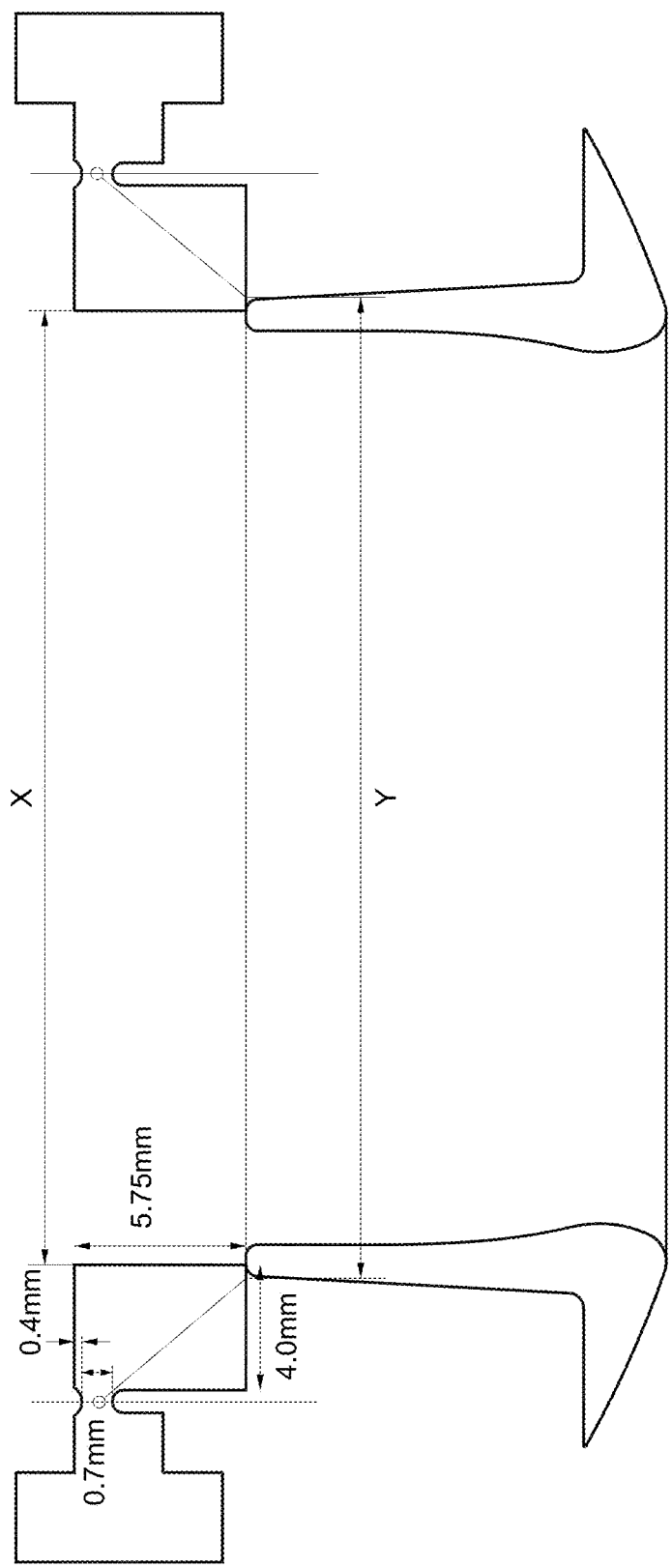
FIG. 11 illustrates dimensions of an example embodiment of the fastener.

FIG. 11 shows example dimensions for one example embodiment of a fastener 140. In the illustrated embodiment, the living hinge has a thickness of 0.7 mm, an upper surface of the living hinge is offset from an upper surface of the moveable portion 144 by 0.4 mm, the moveable portion 144 has a length (measured when the moveable portion 144 is in the neutral position parallel to a central axis through the central opening of the female connector 116) of 5.75 mm, and the moveable portion 144 has a width (measured along the bottom edge 141) of 4.0 mm. As shown in FIG. 10, a width of the living hinge can be 0.75 mm.

To assemble the frame 120 to the housing 114, the male connector 122 is inserted into the female connector 116 so that the male connector 122 engages the fasteners 140. The male connector 122 has a larger external size, e.g., width or diameter, indicated by dimension Y in FIG. 11, than a distance, indicated by X in FIG. 11, between inner edges of the moveable portions 144 of opposing fasteners 140 when the moveable portions 144 are in the neutral position. The larger external size Y of the male connector 122 helps ensure engagement between the male connector 122 and the fasteners 140 during assembly. The values of dimensions X and Y vary depending on the mask. For example, dimensions X and Y will likely be larger for a full-face mask compared to a nasal mask. In some embodiments, Y is between 15 mm and 70 mm. In some embodiments, Y is between 20 mm and 45 mm.

Figure 12A:
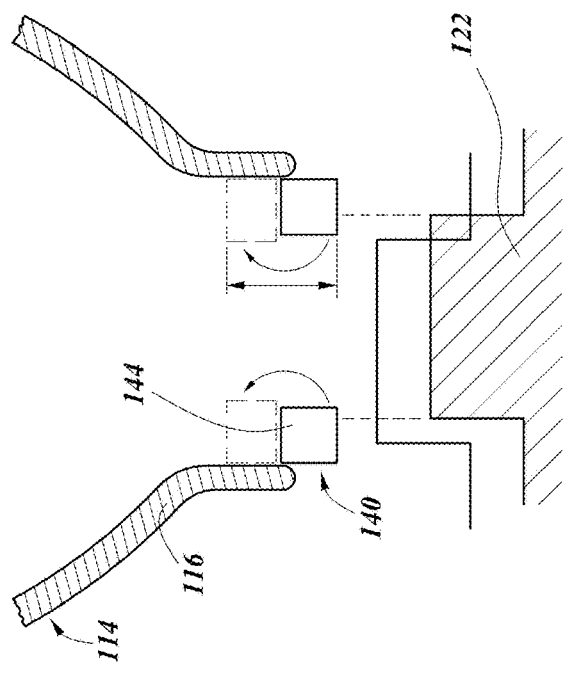
FIGS. 12A-12B illustrate schematics of possible misalignment of the male connector with the fasteners.

FIG. 12A illustrates an embodiment in which the moveable portions 144 are not offset in a rearward direction from the front edge of the female connector 116 and instead protrude forwardly from the housing 114. This embodiment therefore does not include a guide surface to help align the male connector 122 with the moveable portions 144. In such an embodiment, the contact between the male connector 122 and the moveable portions 144 may be asymmetric or misaligned relative to a central axis of the opening of the female connector 116, as shown, and the fasteners 140 may not work as intended or as smoothly as desired. For example, asymmetric or misaligned contact between the male connector 122 and the moveable portions 144 may cause movement of only one of the moveable portions 144 or may cause one moveable portion 144 to begin movement before or after movement of the other movable portion(s) 144. In other words, the asymmetric or misaligned contact can cause timing issues with the movement of the moveable portions 144. If the contact is sufficiently asymmetric or misaligned, such contact may prevent or inhibit at least one moveable portion(s) 144 from being pivoted, and that moveable portion(s) 144 may act to resist engagement of the male connector 122 with the female connector 116. In contrast, when the moveable portions 144 are offset in a rearward direction, the outer surface 123 of the male connector 122 slides along or adjacent the inner surface 119 (FIG. 4) of the female connector 116 as shown in FIG. 5. The guide surface 115 helps guide the male connector 122 into alignment with the moveable portions 144 of the fasteners 140 so that the male connector 122 engages all of the fasteners 140 at the same or approximately the same time and at the same or approximately the same location. This advantageously helps the fasteners 140 function properly. Simultaneous and even contact with all of the fasteners 140 allows the moveable portions 144 to pivot evenly at the same time so that the male connector 122 moves coaxially relative to the female connector 116. This allows each of the moveable portions 144 to apply a relatively equal retention force to the male connector 122 to retain the male connector 122 in a connected and/or assembled configuration with the female connector 166.

Figure 12B:
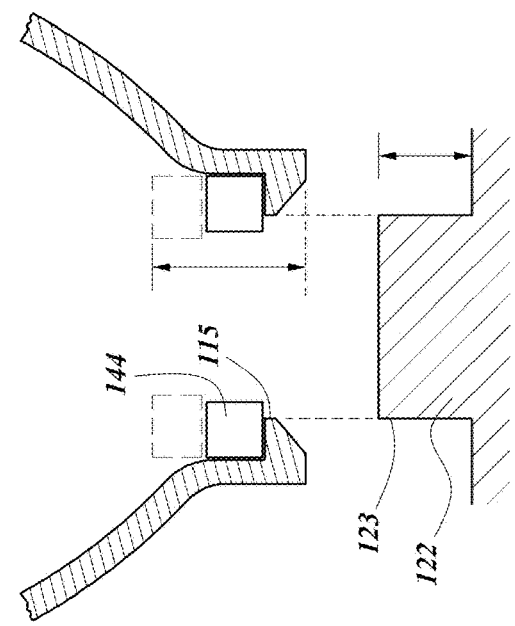
Figure 12C:
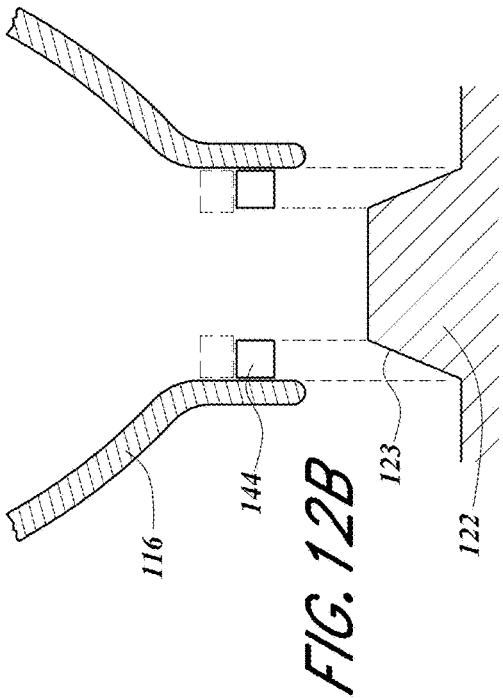
FIG. 12C illustrates a schematic of alignment of the male connector with the fasteners.

In some embodiments, the outer surface 123 of the male connector 122 is relatively straight or non-tapered, for example as shown in FIG. 12C. This can help the male connector 122 slide along the guide surface 115 to help align the male connector 122 into symmetrical alignment with the moveable portions 144 such that all of the moveable portions 144 are engaged and pivoted simultaneously. In contrast, if the outer surface 123 of the male connector 122 is too tapered, for example as shown in FIG. 12B, the male connector 122 could move laterally within the female connector 116, which could cause misalignment of the male connector 122 with the moveable portions 144 and, in some cases, less than optimal operation. However, some amount of taper may be desirable to facilitate coupling of the male connector 122 and the female connector 116. Those skilled in the art can determine an appropriate or desired taper, if any, to address the competing concerns described above. For example, one skilled in the art may consider mold tool geometry (e.g., the draft angle for part removal from tools), part thickness and tolerances, and/or overall geometry in determining an appropriate or desired taper.

Figure 8:
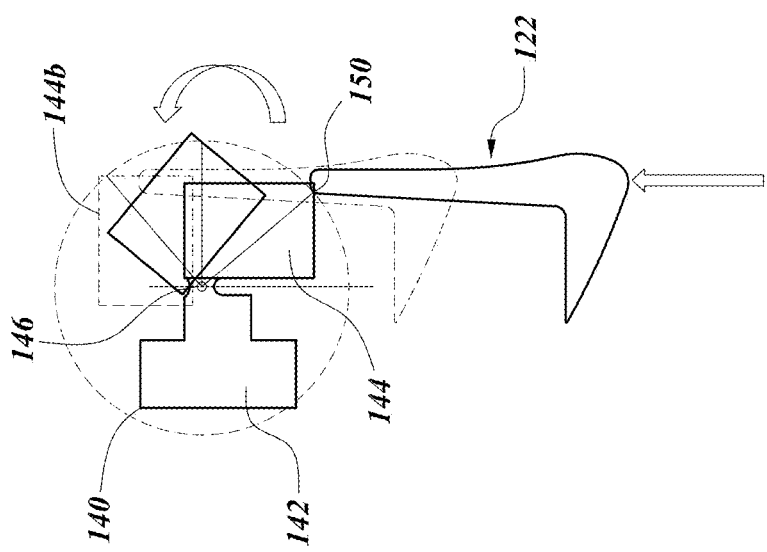
FIG. 8 shows a schematic view of a portion of the male connector of FIG. 5 causing a moveable portion of the fastener of FIG. 7 to change orientation during insertion of the male connector into the housing.
Figure 9D:
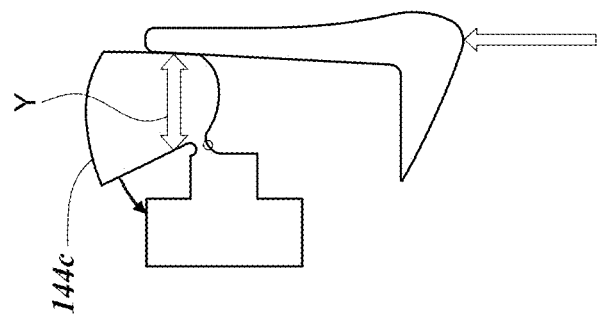
FIGS. 9A, 9B, 9C and 9D illustrate rotation and compression of the moveable portion during various stages of insertion of the male connector into the housing.

When the male connector 122 has been advanced into the female connector 116 by distance D, the leading edge of the male connector 122 contacts the lip 148 of the fastener 140 at a contact point 150 (shown in FIG. 8), as shown in FIG. 5 and in FIGS. 7-8 with the housing 114 not shown. In the illustrated arrangement, the contact point 150 is offset from an inner edge 143 of the moveable portion 144 as shown. This offset helps ensure that engagement of the male connector 122 with the moveable portion 144 applies a rotational force to the moveable portion 144. As the male connector 122 is further advanced into the female connector 116, the male connector 122 causes the moveable portion 144 to rotate or pivot about the hinge point 146, for example as shown in FIGS. 8-9D. In at least some configurations, the male connector 122 contacts the same or approximately the same location, i.e., the contact point 150, of the moveable portion 144 during assembly at least until the moveable portion 144 reaches the center, unstable or fully compressed position. In some configurations, the male connector 122 contacts the same or approximately the same location until the moveable portion 144 reaches its final position. In other words, preferably, there is little to no sliding movement of the male connector 122 relative to the moveable portion 144 at least until the moveable portion 144 reaches the center, unstable or fully compressed position. However, in other configurations, sliding movement prior to the center, unstable or fully compressed position may be desirable. In some embodiments, there is sliding movement of the male connector 122 relative to the moveable portion 144 before and/or after pivoting of the moveable portion 144 from the neutral position to the toggled position. For example, the male connector 122 may slide relative to the moveable portion 144 before engaging the appropriate contact point 150 of the moveable portion 144 to initiate pivoting of the moveable portion 144. As another example, in some embodiments, once the moveable portion 144 has reached its final toggled position, the male connector 122 may be pushed further into the female connector 116 to fully engage the male connector 122 with the female connector 116, and the male connector 122 may therefore slide relative to the moveable portion 144. Such pre- and/or post-pivoting sliding of the male connector 122 relative to the movable portion 144 can advantageously help, for example, properly align of the male connector 122 with the moveable portions 144 and/or soften tolerances.

The mask may comprise at least one alignment feature 151 adapted to align or guide the second connector 122, preferably the male connector, into the first connector 116, preferably the female connector, during assembly. For example, the at least one alignment feature 151 may form part of the moveable portion 144 of the fastener 140. The at least one alignment feature 151 may be in the form of a lug, flap, finger, wing, portion or protrusion or any other form adapted to guide the first and second connectors 116,122 into alignment, for example, to bring the frame 120 into alignment with the fastener 140.

Figure 13:
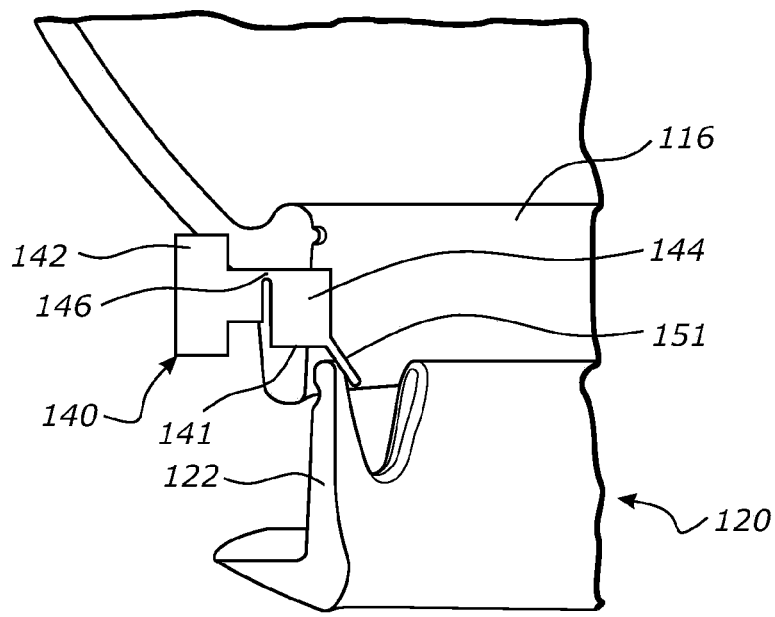
FIG. 13 shows a perspective view of part of a mask in accordance with an embodiment of the invention in which the moveable portion of the mask comprises an alignment feature.
Figure 14:
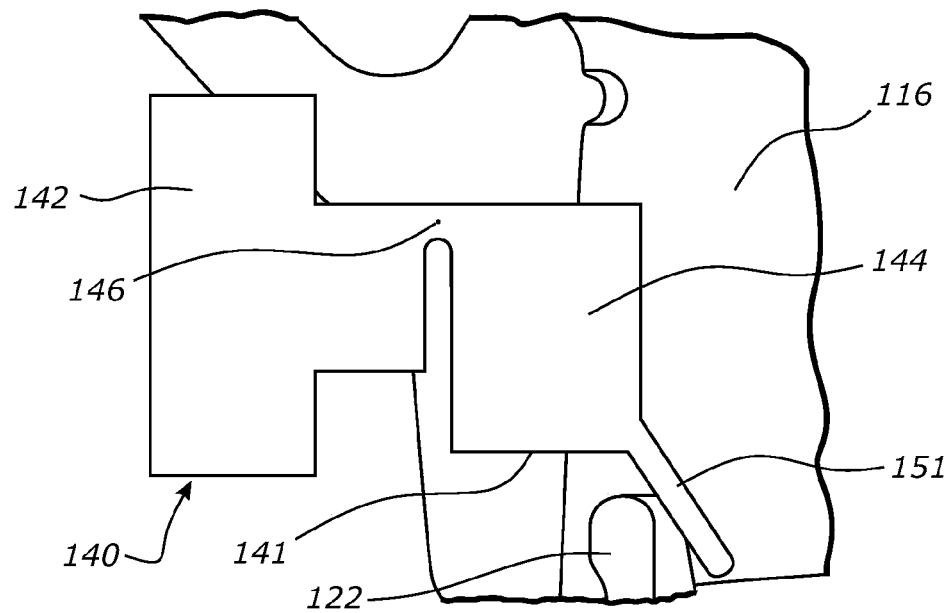
FIG. 14 shows a perspective view of the embodiment shown in FIG. 13.

FIGS. 13 and 14 show an embodiment in which the mask comprises a first female connector 116 and a second male connector 122. The female connector 116 comprises a fastener 140. The fastener 140 comprises a base portion 142 secured to the female connector 116 and a moveable portion 144 which is pivotable about a hinge point 146. The moveable portion 144 comprises an alignment feature 151, in the form of a lug, flap, finger, wing, portion or protrusion. The alignment feature 151 may project or extend at an angle from the moveable portion 144. For example, the alignment feature 151 may extend from an inner and/or lower surface of the female connector 116. For example, the alignment feature 151 may extend inwardly from an inner surface of the female connector 116. The alignment feature 151 may extend at angle of between 95° and 175° from a lower surface of the moveable portion 144. The alignment feature 151 guides the male connector 122 into alignment with the fastener 140 to facilitate assembly of the mask. The alignment feature 151 can guide the male connector 122 into even engagement with a plurality of fasteners 140 arranged about the female connector 116.

The female connector 116 comprises an interior and the alignment feature 151 may comprise an inner surface, facing into the interior of the female connector 116, and an outer surface, facing away from the interior of the female connector 116. The male connector 122 may also comprise an inner surface, facing into the interior of the female connector 116, and an outer surface, facing away from the interior of the female connector 116. As shown in FIGS. 13 and 14, the inner surface of the male connector 122 may contact the outer surface of the alignment feature 151 when the male connector 122 has been advanced into the female connector 116, thereby guiding the first and second connectors 116,122 into alignment. The angle of the outer surface of the alignment feature 151 guides the male connector 122 into contact with a lower surface or bottom edge 141 of the moveable portion 144. The alignment feature 151 is inclined relative to the moveable portion 144 and acts as a ramp or lead in such that the male connector 122 can slide along an outer surface of the alignment feature 151 and into contact with a lower surface of the moveable portion 144, when the male connector 122 is pushed towards the female connector 116. This helps axially align the male connector 122 with the fastener 140 and the female connector 116.

The alignment feature 151 extends inwards towards the interior of the female connector 116 to provide a reduced clearance distance between the moveable portion 144 and opposing side of the female connector 116 or an opposing fastener 140. The clearance distance between innermost tips or edges of opposing alignment features 151 can be less than an external dimension of the male connector 122 and such that interference or engagement between the moveable portion 144 and the male connector 122 is increased. The alignment feature 151 can act as a catch that ensures contact between the male connector 122 and the moveable portion 144 when the male connector is misaligned within the female connector 116.

In various embodiments the alignment feature 151 may extend from a part of the moveable portion 144. FIGS. 15A and B show embodiments of the alignment feature 151 shown in FIGS. 13 and 14. The alignment feature 151 may extend at an angle from the bottom edge 141, lower surface or a lower internal corner of the moveable portion 144 (as shown in FIG. 15A) or from the side or internal surface of the moveable portion 144 (as shown in FIG. 15B).

It will be understood by a person skilled in the art that the alignment features 151 shown in FIGS. 13 to 15 may be incorporated into any one of the other embodiments described herein.

In some embodiments the mask may comprise more than one alignment feature, for example 1, 2, 3, 4, 5, 6 or more alignment features and suitable ranges may be selected from any of these values, for example 1 to 6, 1 to 5 or 1 to 3 alignment features 151, preferably 1 or 2 alignment features 151. In embodiments where the mask comprises more than one alignment feature 151, each alignment feature 151 may be located equidistant from each other alignment feature 151.

The male connector 122 is concentrically aligned with or received within the female connector 116, which restricts non-axial movement of the male connector 122. Therefore, the male connector 122 also compresses and distorts the moveable portion 144, such that when the male connector 122 is fully inserted into the female connector 116, the moveable portion 144 assumes a position and shape approximately indicated by outline 144c in FIG. 6. Whereas if the moveable portion 144 was able to rotate or pivot freely without any constraints, the moveable portion 144 could assume the position and shape approximately indicated by outline 144b in FIGS. 5-6, due to the relative positions and sizes of the male connector 122, female connector 116, and fastener 140, the moveable portion 144 assumes the compressed shape and position approximately indicated by outline 144c when the male connector 122 is fully inserted in the female connector 116. In the illustrated embodiment, the moveable portion 144 is compressed between the male connector 122 and the rib 113 and/or hinge 146. In an embodiment in which the fastener 140 includes only the moveable portion 144, insertion of the male connector 122 into the female connector 116 can cause the moveable portion 144 to change orientation from the neutral orientation to the toggled orientation and compress.

Figure 9C:
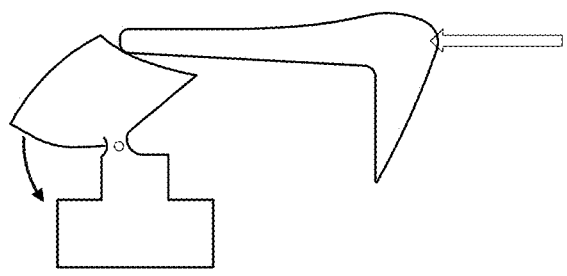
Figure 9B:
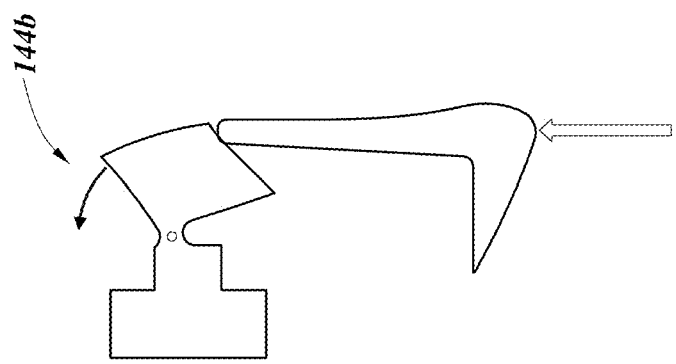
Figure 9A:
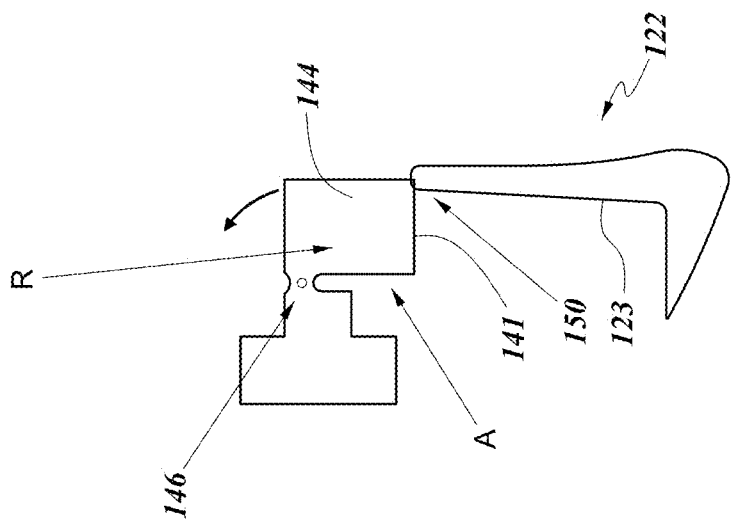

FIGS. 9A-9D illustrate movement and compression of the moveable portion 144 during assembly. FIGS. 9AA-9DD also illustrate movement and compression of the moveable portion 144 during assembly, with FIGS. 9AA-9DD also showing the uncompressed toggled position that the moveable portion 144 could achieve without any constraints in dashed lines 144b, and FIGS. 9BB-9DD also showing the neutral orientation in dashed lines for reference. Outline 122f in FIGS. 9BB and 9CC indicates the final position of the male connector 122 when the male connector 122 is fully engaged or inserted into the cushion module 110. As shown in FIGS. 9A and 9AA, when the male connector 122 initially contacts the moveable portion 144, the moveable portion 144 is in the neutral orientation and is not compressed. As the male connector 122 is advanced further into the female connector 116 as shown in FIGS. 9B-9C and 9BB-9CC, the moveable portion 144 pivots or rotates and compresses between the male connector 122 and the female connector 116. The amount of compression increases as the male connector 122 moves from the position of FIG. 9B to that of FIG. 9C, as indicated by the increase in distance x in FIG. 9CC compared to FIG. 9BB. In FIGS. 9AA-9DD, line R indicates the distance between the contact point 150 and the hinge point 146 as the toggle portion pivots about the hinge point 146. A dashed circle in each of these figures indicates the trajectory of the contact point 150 if the moveable portion 144 were pivoted but not compressed. The amount of compression (e.g., radial compression), distance x, that the moveable portion 144 experiences is measured along the line R. Distance x is the difference between the location of the contact point 150 when the moveable portion 144 is compressed and the trajectory of the contact point if the moveable portion 144 was not compressed. An angle between line R and a line A extending through the hinge point 146 parallel to the direction of movement of the male connector 122 is the angle of rotation of the moveable portion 144. The amount of interference between the moveable portion 144 and the male connector 122 varies depending at least in part on the angle of rotation of the moveable portion 144.

The amount of compression x during assembly is greatest in the position of FIG. 9C. This position is the peak or an unstable equilibrium position of the bistable or over-centre moveable portion 144. In other words, this compression of the moveable portion 144 causes the moveable portion 144 to want to pivot to either the neutral position or toggled position to relieve the compression. Continued advancement of the male connector 122 urges the moveable portion 144 toward the toggled position. The user may experience a bump or snap sensation as the male connector 122 is advanced from the position of FIG. 9C to the final position of FIG. 9D as a result of the reduction in compression (indicated by the decrease in distance x of FIG. 9D compared to 9C). When the bottom edge 141 of the moveable portion 144 comes into parallel contact with the outer surface 123 of the male connector 122, as shown in FIG. 9D, lateral compression of the moveable portion 144 provides a retention force on the male connector 122, indicated by arrow y in FIG. 9D. The compressed moveable portion 144 attempts to return to its uncompressed state and applies a force to the outer surface of the male connector 122. This force retains or fastens the frame 120 to the housing 114. In other configurations, the compression could remain approximately constant or could increase from the peak position to the toggled position and the fastener 140 could rely on the over-centre geometry and/or shape to remain the in the toggled or assembled position.

FIG. 10 shows lateral compression c relative to the angle of rotation for an example embodiment of the fastener 140. In this embodiment, the distance along line R between the hinge point 146 and the initial contact point 150 of the moveable portion 144 with the male connector 122 is 6.316 mm. If the moveable portion 144 was pivoted to the toggled position without compression, this value would remain constant through rotation. The distance of travel of the male connector 122 from initial contact with the moveable portion 144 to complete insertion into the female connector 116 is 8.86 mm. In this embodiment, the contact point 150 is offset from the inner edge 143 of the moveable portion 144 by 0.75 mm. The lateral compression c (which also equals compression x) in the position of FIG. 9C for this embodiment is 1.33 mm. The lateral compression c at the toggled position can be 1.12 mm. This dimension can be converted to compression x with consideration of the angle at the toggled position. However, it is apparent that the compression of the moveable portion 144 is reduced between the peak position and the toggled position.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A cushion module for a respiratory mask comprising:
a cushion configured to seal on a user's face in use; and
a housing coupled to the cushion, the housing comprising:
a connector defining an opening, the connector configured to connect to another component of the respiratory mask;
at least one alignment feature that aligns or guides the another component of the respiratory mask into the connector during assembly; and
at least one fastener configured to fasten the cushion module to the another component, each fastener comprising:
a base portion fixed to the cushion module; and
a moveable portion pivotally coupled to the base portion via a joint,
wherein the moveable portion is configured to toggle about the joint from a neutral orientation to a locked orientation when the another component is coupled to the connector, and wherein in the locked orientation, the moveable portion applies a retention force to the another component to secure the another component to the connector.

2. The cushion module for the respiratory mask of claim 1, wherein the moveable portion is made of a resiliently deformable material, the moveable portion is configured to be compressed as the moveable portion is pivoted from the neutral orientation to the locked orientation, and compression of the moveable portion provides the retention force to the another component.

3. The cushion module for the respiratory mask of claim 2, wherein the moveable portion is more compressed in an intermediate orientation between the neutral orientation and the locked orientation than in both the neutral orientation and the locked orientation.

4. The cushion module for the respiratory mask of claim 2, wherein the moveable portion is more compressed in the locked orientation than in the neutral orientation.

5. The cushion module for the respiratory mask of claim 1, wherein the at least one fastener is a plurality of fasteners spaced about the opening of the connector.

6. The cushion module for the respiratory mask of claim 5, wherein a distance between an inner surface of the moveable portion of a first fastener of the plurality of fasteners and an inner surface of the moveable portion of a second fastener of the plurality of fasteners that is disposed opposite the first fastener across the opening is less than a width of a second connector of the another component.

7. The cushion module for the respiratory mask of claim 1, wherein the moveable portion is biased toward the neutral orientation.

8. The cushion module for the respiratory mask of claim 1, wherein the joint comprises a living hinge.

9. The cushion module for the respiratory mask of claim 8, wherein the living hinge comprises a thinned portion of material extending between the base portion and the moveable portion.

10. The cushion module for the respiratory mask of claim 1, wherein the base portion and the moveable portion are integrally formed.

11. The cushion module for the respiratory mask of claim 1, wherein the moveable portion comprises a contact point spaced from the joint, the contact point configured to be engaged by the another component when the another component is coupled to the connector.

12. The cushion module for the respiratory mask of claim 11, wherein a distance between the joint and the contact point in the neutral orientation is greater than the distance in an intermediate orientation between the neutral orientation and the locked orientation and greater than or equal to the distance in the locked orientation.

13. The cushion module for the respiratory mask of claim 12, wherein the distance in the intermediate orientation is less than the distance in the locked orientation.

14. The cushion module for the respiratory mask of claim 1, wherein a distal edge of the moveable portion that faces a mouth of the opening and is configured to contact a second connector of the another component is flat.

15. The cushion module for the respiratory mask of claim 1, wherein the connector comprises a generally cylindrical female connector, the another component comprises a frame and a second connector, the second connector comprising a generally cylindrical male connector configured to be received in the generally cylindrical female connector.

16. The cushion module for the respiratory mask of claim 15, wherein the base portion is overmolded to the housing.

17. A cushion module for a respiratory mask comprising:
a cushion configured to seal on a user's face in use; and
a housing coupled to the cushion, the housing comprising:
   a connector defining an opening, the connector configured to connect to another component of the respiratory mask;
   at least one alignment feature that aligns or guides the another component of the respiratory mask into the connector during assembly; and
   at least one fastener configured to fasten the cushion module to the another component, wherein the at least one fastener is configured to toggle from a neutral orientation to a locked orientation when the another component is coupled to the connector, and wherein in the locked orientation, the at least one fastener applies a retention force to the another component to secure the another component to the connector.

18. The cushion module for the respiratory mask of claim 17, wherein the at least one fastener is made of a resiliently deformable material, the at least one fastener is configured to be compressed as the at least one fastener is pivoted from the neutral orientation to the locked orientation, and compression of the at least one fastener provides the retention force to the another component.

19. The cushion module for the respiratory mask of claim 18, wherein the at least one fastener is more compressed in an intermediate orientation between the neutral orientation and the locked orientation than in both the neutral orientation and the locked orientation.

20. The cushion module for the respiratory mask of claim 18, wherein the at least one fastener is more compressed in the locked orientation than in the neutral orientation.

21. The cushion module for the respiratory mask of claim 17, comprising a plurality of fasteners spaced about the opening of the connector.

22. The cushion module for the respiratory mask of claim 21, wherein a distance between an inner surface of a first fastener and an inner surface of a second fastener that is disposed opposite the first fastener across the opening is less than a width of a second connector of the another component.

23. The cushion module for the respiratory mask of claim 17, wherein the connector comprises a generally cylindrical female connector, the another component comprises a frame and a second connector, the second connector comprising a generally cylindrical male connector configured to be received in the generally cylindrical female connector.

* * * * *